US012232996B2

(12) United States Patent
Young et al.

(10) Patent No.: US 12,232,996 B2
(45) Date of Patent: Feb. 25, 2025

(54) PATIENT STABILIZATION AND SECURING DEVICE FOR ROBOTIC AND LAPAROSCOPIC SURGERIES IN TRENDELENBURG POSITION

(71) Applicant: The Board of Trustees of the University of Illinois, Urbana, IL (US)

(72) Inventors: Michael J. Young, Urbana, IL (US); Craig Niederberger, Urbana, IL (US); Stephan Peter Pfanner, Urbana, IL (US); Andrew Graham, Urbana, IL (US); Julissa Garcia, Urbana, IL (US); Sweta Shah, Urbana, IL (US); Leigha Covnot, Urbana, IL (US); Zahra Ahsan, Urbana, IL (US); Kimberlee Wilkens, Urbana, IL (US); Cristian Luciano, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 731 days.

(21) Appl. No.: 17/049,796

(22) PCT Filed: Apr. 26, 2019

(86) PCT No.: PCT/US2019/029495
§ 371 (c)(1),
(2) Date: Oct. 22, 2020

(87) PCT Pub. No.: WO2019/210274
PCT Pub. Date: Oct. 31, 2019

(65) Prior Publication Data
US 2021/0236322 A1    Aug. 5, 2021

Related U.S. Application Data

(60) Provisional application No. 62/663,266, filed on Apr. 27, 2018.

(51) Int. Cl.
*A61F 5/37* (2006.01)
*A61G 13/04* (2006.01)

(52) U.S. Cl.
CPC ............ *A61F 5/3784* (2013.01); *A61G 13/04* (2013.01)

(58) Field of Classification Search
CPC .......... A61F 5/3769–3784; A61F 5/37; A61G 13/00; A61G 13/02; A61G 13/04;
(Continued)

(56) References Cited

U.S. PATENT DOCUMENTS 4,699,132 A    10/1987 Carville
5,183,007 A *   2/1993 Vincent ................. A61F 5/3784
                                                          119/857
(Continued)

FOREIGN PATENT DOCUMENTS

CN    202723248 U  *  2/2013
EP       2988717 B1     2/2019

OTHER PUBLICATIONS

Brochure for "Safe-T-Secure" "Trendelenburg positioning solution" which cites U.S. Pat. No. 10,512,578 and EP Pat. No. 2,988,717, obtained by inventors on or before Aug. 18, 2024.

*Primary Examiner* — Michelle J Lee
(74) *Attorney, Agent, or Firm* — McDonnell Boehnen Hulbert & Berghoff LLP

(57) ABSTRACT

The present application is directed to a method and system for restraining a patient before, during, or after surgery that increases efficiency of the surgical setup process and minimizes risk of musculoskeletal damage to the patient, particularly in surgeries requiring a patient to be in a Trendelenburg position (e.g., robotic or laparoscopic surgeries). One or more restraints can be worn by a patient prior to surgery', and may function to redistribute the patient's weight across the patient's torso to reduce strain on the patient's shoulders and back. The restraint(s) can be attached to a surgical table by way of an attachment mechanism coupled to the restraint(s) and the table. The attachment mechanism can secure the patient to the table by way of one or more straps, clips, and/or other intermediates. Optionally, the restraint(s) can fulfill other surgical needs, such as heat regulation and vascular compression.

18 Claims, 6 Drawing Sheets

(58) Field of Classification Search
CPC .......... A61G 13/10; A61G 13/12–1295; A47D 15/00; A47D 15/005–008; A61B 6/04; A61B 6/0407; A61B 6/0421
See application file for complete search history.

(56) References Cited

U.S. PATENT DOCUMENTS

| | | | |
|---|---|---|---|
| 5,433,222 A * | 7/1995 | Boomgaarden | A61G 13/101 24/72.5 |
| 6,149,674 A * | 11/2000 | Borders | A61G 13/02 607/104 |
| 10,512,578 B2 | 12/2019 | VIsco | |
| 2005/0126578 A1 | 6/2005 | Garrison et al. | |
| 2010/0224200 A1* | 9/2010 | Kopczynski | A47D 15/008 128/870 |
| 2010/0275377 A1 | 11/2010 | West | |
| 2011/0000494 A1 | 1/2011 | Soung | |
| 2011/0296609 A1 | 12/2011 | Giap | |
| 2011/0314585 A1 | 12/2011 | Blakely et al. | |
| 2012/0255124 A1* | 10/2012 | West | A61B 46/20 5/623 |
| 2013/0192608 A1* | 8/2013 | Hiebert | A61G 13/1275 128/845 |
| 2013/0327339 A1* | 12/2013 | Chua | A61G 13/04 128/845 |
| 2014/0352072 A1* | 12/2014 | Holladay | A61G 13/126 5/655.5 |
| 2016/0279007 A1 | 9/2016 | Flatt | |

* cited by examiner

PATIENT STABILIZATION AND SECURING DEVICE FOR ROBOTIC AND LAPAROSCOPIC SURGERIES IN TRENDELENBURG POSITION

CROSS-REFERENCE TO RELATED APPLICATIONS

This application claims priority to U.S. Patent Application Ser. No. 62/663,266 filed on Apr. 27, 2018, which is hereby incorporated by reference in its entirety.

This application is the US national phase under 35 U.S.C. § 371 of International Application No. PCT/US2019/029495, filed Apr. 26, 2019, which claims priority to U.S. Patent Application Ser. No. 62/663,266 filed on Apr. 27, 2018, which are hereby incorporated by reference in their entirety.

BACKGROUND

Robotic surgery is a minimally invasive method of performing surgery via small incisions in the skin, rather than larger openings typical of standard surgical procedures. Recent advents in robotic surgery have focused on improving the patient experience by minimizing scarring and trauma on a patient's body, thereby providing a faster recovery time. Laparoscopic surgery, also referred to as minimally invasive surgery, is defined by the use of small instruments and a camera to perform surgical procedures, and provides similar advantages to robotic surgery. In both techniques, smaller surgical incisions are used to mitigate blood loss, reduce postoperative pain, and provide faster recovery times for patients. Surgeons are also better able to control the surgical environment, making it safer for the patient and time-effective for the surgeon and hospital.

During such surgical procedures, patients can be placed on an operating table in the Trendelenburg position, wherein the patient's body is laid supine on an incline with the feet elevated above the head. The Trendelenburg position generally requires patients to be positioned on an operating table angled between 15-30 degrees, however certain procedures can require inclines of up to 45 degrees.

In general, laparoscopic and robotic surgeries begin by preparing the operating room and laying a conscious patient supine onto the operating table. The patient is then placed under anesthesia, and the unconscious patient is secured into the Trendelenburg position, with their feet elevated above the head. Currently, patients are maintained in the Trendelenburg position through the use of shoulder pad apparatuses, gel pads, memory foam, belt straps, tape, and other instruments. The stabilization methods used are often informal and ad-hoc. Securing a patient in the Trendelenberg position generally takes between 30 minutes and an hour to complete while the patient is under anesthesia, and could take even longer depending on the weight and stature of the patient. This is an inefficient use of time for hospital staff, and a waste of money for hospitals.

Because the current standard of care lacks a clear procedure or device for maintaining a patient in an inclined position, the surgical setup is imprecise and time-consuming and the patient risks life-threatening injuries due to slipping and movement during surgery. Even when the patient is positioned securely, back and shoulder pain is common due to poor weight distribution provided by informal supporting apparatuses.

SUMMARY

The present application generally relates to a method and system for restraining a patient before, during, or after surgery that increases the efficiency of the surgical setup process and minimizes risk of musculoskeletal damage to the patient. As provided herein, such a system can include an upper body restraint, an attachment mechanism and, optionally, a lower body restraint. When wearing the restraints, a patient can be restrained to a table (e.g., a surgical table) by coupling the attachment mechanism to the restraints and the table.

In a first implementation, a system is provided. The system includes an upper body restraint configured to surround at least a portion of a chest of the patient. The upper body restraint includes a securing mechanism and a supporting portion. The securing mechanism reversibly locks such that the chest of the patient is reversibly secured within the upper body restraint. The supporting portion is configured to distribute weight of the patient across a torso of the patient. The system further includes an attachment mechanism coupled to the upper body restraint for selectively securing the upper body restraint and to a table. The upper body restraint reversibly secures the patient to the table. When the attachment mechanism is connected to the upper body restraint and the table, the patient's abdomen is in a fixed position on the table.

In a second implementation, a method is provided. The method includes configuring a device for securing at least a portion of a chest of a patient into an upper body restraint. The upper body restraint includes a securing mechanism and a supporting portion. The securing mechanism is configured to reversibly lock such that the chest of the patient is secured within the upper body restraint. The supporting portion is configured to distribute weight of the patient across a back of the patient. The method further includes configuring a device for securing at least a portion of a leg of a patient into a lower body restraint. The lower body restraint is coupled to the upper body restraint. The method also includes configuring a device for restraining the patient to a table by way of an attachment mechanism that positions the patient on the table in a fixed position. The attachment mechanism is removably attachable to at least one of the upper body restraint, the lower body restraint, and the table.

In a third implementation, a system is provided. The system includes a harness configured to selectively secure a patient to an operating table. The harness includes selectively removable sections.

In a fourth implementation, a method is provided. The method includes providing one or more restraining portions. The method also includes providing a supporting portion. Providing the supporting portion includes arranging a plurality of supporting members in a cross-cross pattern. The method further includes providing a securing mechanism configured to reversibly couple with the one or more restraining portions. The method also includes affixing the supporting portion and the securing mechanism to the one or more restraining portions to form an upper body restraint configured to surround at least a portion of a chest of a patient. The supporting portion is positioned whereby the supporting members are arranged in a criss-cross pattern across the patient's back. The one or more restraining portions extend around the patient and converge at the securing mechanism. The method further includes providing an attachment mechanism connectable to the upper body restraint and a table. The upper body restraint reversibly secures the patient to the table wherein the chest of the patient is in a fixed position relative to the table when the attachment mechanism is coupled to the upper body restraint and the table.

DETAILED DESCRIPTION

This application is directed to a methods and systems for restraining a patient before, during, or after surgery that increases surgical setup efficiency and minimizes risk of musculoskeletal damage, particularly in surgeries requiring a patient to be in a Trendelenburg position (e.g., robotic or laparoscopic surgeries).

Exemplary methods and systems are described herein. It should be understood that the word "exemplary" is used herein to mean "serving as an example, instance, or illustration." Any embodiment or feature described herein as "exemplary" or "illustrative" is not necessarily to be construed as preferred or advantageous over other embodiments or features. More generally, embodiments described herein are not meant to be limiting. It will be readily understood that certain aspects of the disclosed methods and systems can be arranged and combined in a wide variety of different configurations, all of which are contemplated herein.

As used herein, the term "strap" generally refers to a tensile member, for instance, a flat strap, a cord, a belt, a tube or tubing, a cloth or textile (e.g., rope), a chain or linked member, or some other flexible tensile member. While exemplary embodiments can include flat straps of ballistic nylon, it will be readily understood that "strap" embodiments herein are not intended to be limited to a particular material, dimension, characteristic, or configuration.

While the system is described as being used in relation to robotic and/or laparoscopic surgery taking place on an inclined operating table, it will be readily understood that such a system could be implemented in a variety of different surgical environments. Further, while the term "patient" as used herein generally refers to a human patient, the term could be used interchangeably to mean any human or non-human mammal, or some other unspecified subject.

Restraining systems set forth in this application address a need for a restraining device that is capable of securing a patient on an angled table (e.g., an operating table, a surgical bed, or some other patient-care surface) while supporting the patient's neck, back, and shoulders to minimize musculoskeletal injury. Such a device can be straightforward enough for a patient to use prior to entering an operating room, allowing for more efficient setup once the patient is anesthetized and the surgeon begins surgical preparations. Further, a uniform method for restraining a patient is provided to streamline the Trendelenburg setup process and decrease the risk of patient injury due to slipping and poor weight distribution. Providing a device and method for facilitating the Trendelenburg setup process advantageously minimizes musculoskeletal injury to the patient while saving valuable time in the operating room, thereby reducing surgical costs and patient rehabilitation time.

Example Systems

Figures 1A, 1B:
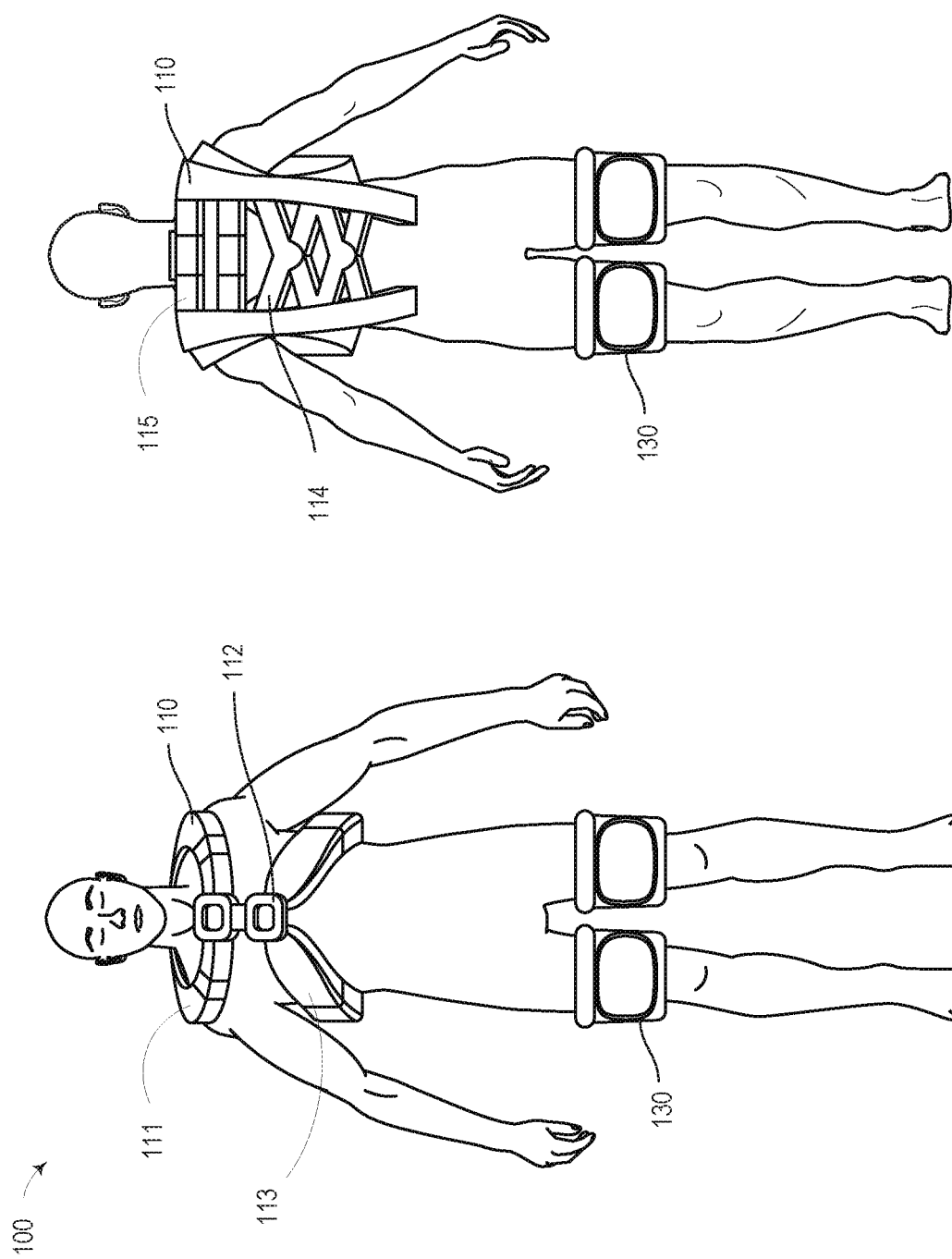
FIG. 1A depicts a front view of an example patient restraint system in accordance with at least one embodiment.
FIG. 1B depicts a back view of the patient restraint system of FIG. 1A in accordance with at least one embodiment.

FIG. 1A depicts a front view of an example patient restraint system 100 in accordance with at least one example embodiment. The system 100 can be used, among other things, for securing a patient to a table before, during, or after a surgical procedure. In one example embodiment, the system 100 can be used for securing a patient in preparation for a surgical procedure requiring the patient to be restrained on an angled operating table.

The system 100 can include an upper body restraint 110 and an attachment mechanism 120 (not visible in FIG. 1). The upper body restraint can reversibly secure a patient to a table, and when the attachment mechanism is connected to the upper body restraint and the table the patient's abdomen is in a fixed position on the table. In some examples, such as the embodiment shown in FIGS. 1A and 1B, the system 100 can further include a lower body restraint 130. The patient restraint system 100 or portions thereof can be worn by a patient prior to entering the surgical environment in order to facilitate securing the patient's body to the operating table after anesthesia and prior to surgery. In use, the upper body restraint 110 can be positioned around the patient's chest, abdomen, neck, shoulders, and arms similarly to a vest, e.g., a floatation vest, or a harness, while optionally leaving the patient's upper extremities uncovered. In other words, the upper body restraint can be configured to surround at least a portion of the patient's chest. As seen in FIGS. 1A-B, the lower body restraint 130 can be configured to surround at least a portion of the patient's leg(s). In certain embodiments, the lower body restraint 130 can be configured as a leg cuff (as pictured in FIGS. 1A-B), a brief-like garment to be worn around the waist or hips, a trunk-like garment that covers a portion of both the patient's waist or hips and the legs, or worn around some other area of the lower body.

In some surgical environments, it can be important for certain portions of the patient's torso to be readily available for surgical access and uncovered by the restraint(s). Accordingly, in some examples the upper body restraint 110 and/or lower body restraint 130 can be configured such that the patient's chest, abdomen, stomach, groin, perineum, or another anatomical area of interest is exposed. Further, the upper body restraint 110 and the lower body restraint 130 can be formed of a variety of materials, for instance, nylon (e.g., ballistic nylon or military grade nylon), elastic spacer mesh, a textile, a polymer, or some other material. Materials of system 100 can be selected to increase patient comfort, to satisfy a desired tensile strength requirement, to permit sterilization, to decrease cost (e.g., so that the restraints and other elements can be disposable), to minimize radiopacity (i.e., so that the patient can undergo an x-ray while wearing the restraints), to reduce electrical conductivity, or for some other desired material characteristic.

While FIGS. 1A-B illustrate the upper body restraint 110 and the lower body restraint 130 as physically separated, an exemplary system 100 provides for coupling between the upper body restraint 110 and the lower body restraint 130 such that the patient's weight can be distributed between the two restraints.

The upper body restraint 110 includes a supporting portion 114 that functions to reduce musculoskeletal trauma to the patient's back and shoulders during surgery, particularly surgeries in which the patient is positioned at an angle that places excess weight onto the patient's back and shoulders, e.g., a Trendelenburg position. The supporting portion 114 can be located proximate to the patient's torso when the upper body restraint 110 is in use, and generally acts to distribute a patient's weight across the patient's torso (e.g., abdomen, trunk, chest, and/or back) to reduce musculoskeletal pain. In some examples, the supporting portion 114 includes a plurality of supporting members (e.g., elastic or inelastic straps and/or other members configured to transfer tension in a longitudinal direction across the members). The supporting members can be generally arranged in a criss-cross pattern across the patient's torso when the upper body restraint 110 is being worn by the patient. In a particular example, as illustrated in the back view of FIG. 1B, the supporting members are arranged in a criss-cross pattern across the patient's back. Any number of desired supporting members can be used, for example, two supporting members arranged in a cross arrangement, four supporting members arranged to form two respective crosses, six supporting members forming three respective crosses, etc. Similarly, the supporting members and larger supporting portion 114 can be formed of any desired material, for instance, nylon (e.g., ballistic nylon or military grade nylon), elastic spacer mesh, a textile, a polymer, or some other material.

In some examples, the upper body restraint 110 includes members, e.g., straps, supports, or other restraining members, that extend from the back of the upper body restraint 110 proximate to the patient's back, around the patient's arms and/or shoulders, and converge proximate to the patient's chest (converging at, e.g., securing mechanism 112). In a particular example, the upper body restraint 110 can be configured similarly to a vest-like garment, including a first restraining portion 111 configured to extend over the patient's shoulders and a second restraining portion 113 configured to extend under the patient's armpits, leaving the patient's upper extremities uncovered. The restraining portions 111, 113 can be configured as straps arranged to surround and hold the patient's chest at a fixed location relative to the upper body restraint 110 and/or the table. While FIG. 1 depicts an upper body restraint 110 as including an upper restraining portion 111 and a lower restraining portion 113, any number of restraining members (i.e., straps or other members extending around a portion of the patient's body) can be envisioned. For instance, in alternative embodiments the upper body restraint 110 includes four restraining members, six restraining members, eight restraining members, or more. Similarly, restraining members can be configured to surround any desired portion of the patient's torso or upper extremities. For instance, restraining members can be provided that surround at least a portion of the patient's arms, chest, head or neck, shoulders, or some other location on the patient's upper body.

The restraining members, supporting portion 114, and/or supporting members thereof can be partially or fully concealed by or contained within an outer body of the upper body restraint 110. The outer body can take the form of an additional textile or garment layer shaped such that the restraining members, supporting portion 114, and/or supporting members maintain their arrangement and are not readily visible and/or accessible to a patient wearing the upper body restraint 110. In some examples, the outer body of the upper body restraint 110 resembles a garment, e.g., a vest, and optionally includes an additional textile or material layer (e.g., a high density foam or elastic spacer mesh) for improved comfort, elasticity, breathability or some other benefit.

At least one securing mechanism 112 can be included in the upper body restraint 110 to facilitate securing and disengagement of the system 100 from the patient's chest. For instance, a patient can desire a straightforward mechanism for securing the upper body restraint 110 without supervision from a medical professional, e.g., if the restraint is intended to be put on by a patient prior to entering the operating room. Similarly, a surgeon or other surgical staff can desire a simple disengagement mechanism for removing the upper body restraint 110 from the patient while the patient is unable to assist, e.g., while the patient is under anesthesia, during or after a surgical procedure, or in case of a medical emergency.

The securing mechanism 112 reversibly locks the upper body restraint 110 (and/or restraining portions thereof) such that the patient is reversibly secured within the upper body restraint 110. For instance, the securing mechanism 112 can be configured to reversibly couple with one or more restraining portions and/or restraining members of the device (i.e., secure or lock itself in connection with the restraining portions or members). When the upper body restraint is secured using the securing mechanism 112, the patient's body is generally fixed relative to the upper body restraint 110 and/or the table. In various embodiments, the securing mechanism 112 includes a releasable buckle, such as a multiple-point buckle (e.g., a three point, four point, or five point buckle or the like), a plastic buckle (i.e., a plastic buckle similar to a buckle found on a book bag or luggage), a loop connector, a non-conductive fastener, a hook-and-loop fastener, a snap fit connector, a parachute clip, or some other reversible securing mechanism. In some examples, the securing mechanism 112 is configured with additional protection mechanisms to prevent unintended disengagement of the securing mechanism. For instance, the securing mechanism 112 can require activation by two hands, can include a child protection lock, or can require use of a key or some other disengagement instrument.

In some examples, the securing mechanism 112 is included in a front portion of the upper body restraint 110, proximate to a patient's chest or shoulders. In a specific example, the upper body restraint 110 comprises a first restraining portion 111 configured to extend over the patient's shoulders and a second restraining portion 113 configured to extend under the patient's armpits, wherein the first and second restraining portions 111, 113 converge on the securing mechanism 112. However, the securing mechanism 112 can be arranged at any desired location. For instance, the securing mechanism 112 can be arranged proximate to at least one side of the patient (e.g., near a patient's ribcage), proximate the patient's back, or at some other easily accessible location when the patient is positioned in an inverted and/or angled position on a table.

In order to be adaptable to fit a variety of patients, portions of the upper body restraint 110 can be adjustable to increase or decrease the size of the upper body restraint 110. For instance, restraining members of the upper body restraint 110 can be configured to be adjustable by way of and adjustable-length strap featuring a slide adjuster or some other adjustment mechanism. As seen in FIG. 1B, in some embodiments, an adjustable shoulder portion 115 can be provided on the upper body restraint 110, and can include at least one adjustable strap to increase or decrease a shoulder span of the upper body restraint 110. Additionally or alternatively, the upper body restraint 110 can be provided in discrete sizes to fit a variety of patients (e.g., small/medium/large, adult/youth, or some other discrete sizing scheme).

As shown in FIGS. 1A-B, the lower body restraint 130 can be generally configured as one or more cuffs to be worn around a patient's leg. In various embodiments, the lower body restraint 130 includes a cuff sized to be worn around a patient's thigh, calf, ankle, or another portion of a leg. Beneficially, restraining the patient at their legs provides a means of securing the patient to the table without obstructing access to surgical target areas such as the patient's abdomen, stomach, groin, or perineum. This can be particularly advantageous for surgeries requiring a patient's legs to be in an apart or open position. However, other configurations of the lower body restraint 130 are possible. While FIGS. 1A-B generally show the lower body restraint 130 as a pair of leg cuffs, in some examples the lower body restraint is configured to surround at least a portion of a patient's waist, hips, or groin, and can be shaped similarly to, e.g., a trunk, boxer brief, brief, or compression shorts.

To provide equal distribution of the patient's weight into the restraints, the lower body restraint 130 can be configured to connect to the upper body restraint 110. When the lower body restraint is connected to the upper body restraint whereby the leg of the patient is in a fixed position on the table (i.e., such that when the attachment mechanism is connected to the upper body restraint and the table the lower body restraint additionally secures the patient's leg to the table). Coupling can be achieved by way of one or more straps or other tensile members extending between the lower body restraint 130 and the upper body restraint 110. Such straps can be formed of similar materials to the restraints, e.g., ballistic nylonn, elastic spacer mesh, or some other material. In some embodiments, the upper body restraint 110 and/or the lower body restraint 130 are formed as an integrated full-body restraint configured to surround at least a portion of the patient's torso, and legs, and/or optionally the patient's chest, abdomen, shoulders, stomach, hips, waist, or groin, while leaving any desired surgical target areas unobstructed. Such a full-body restraint can be additionally concealed by or contained within an outer body portion (i.e., an additional textile or garment layer) to facilitate putting on the device and/or improve patient comfort.

Figure 2:
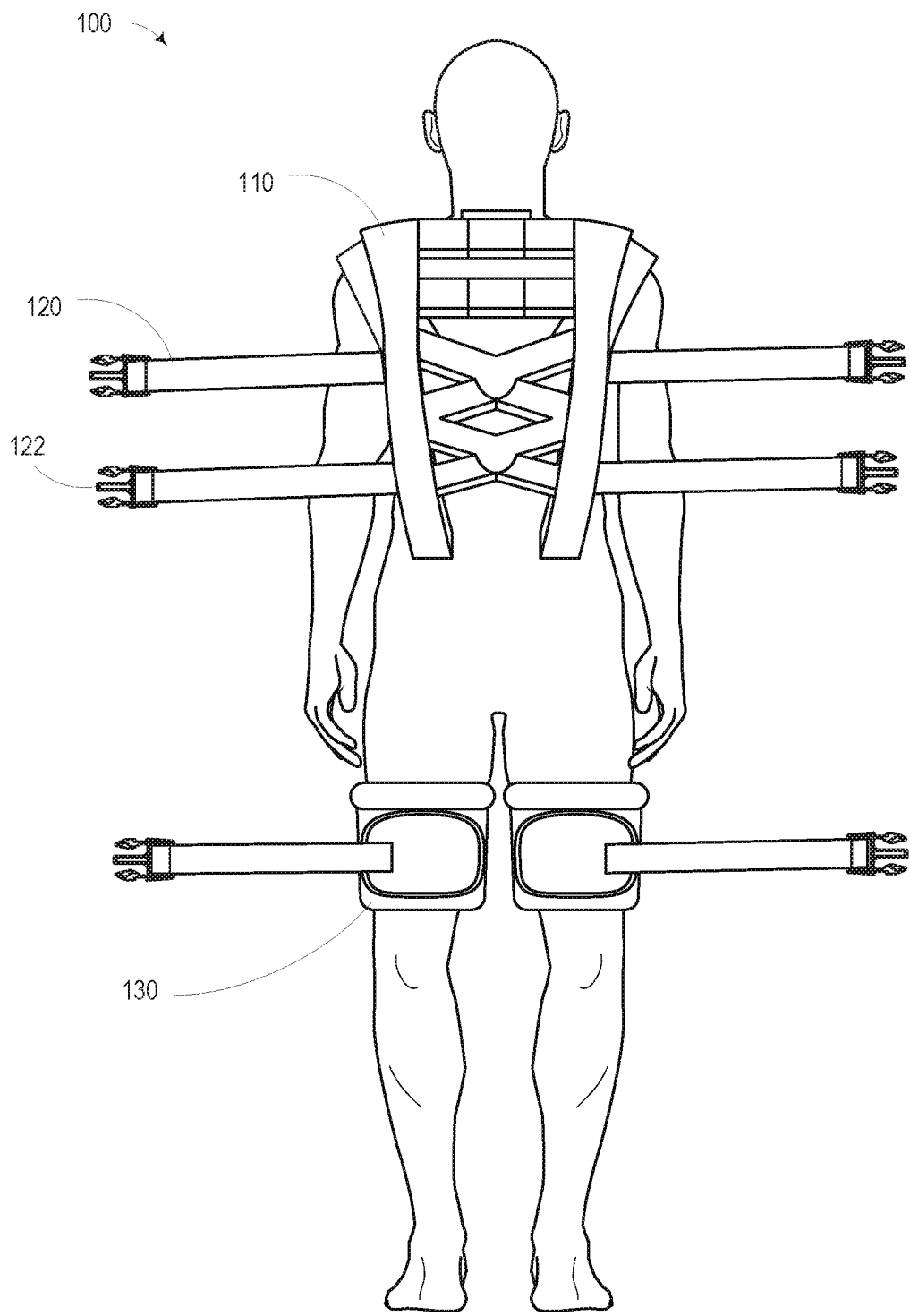
FIG. 2 depicts an example patient restraint system including an attachment mechanism in accordance with at least one embodiment.
Figure 3:
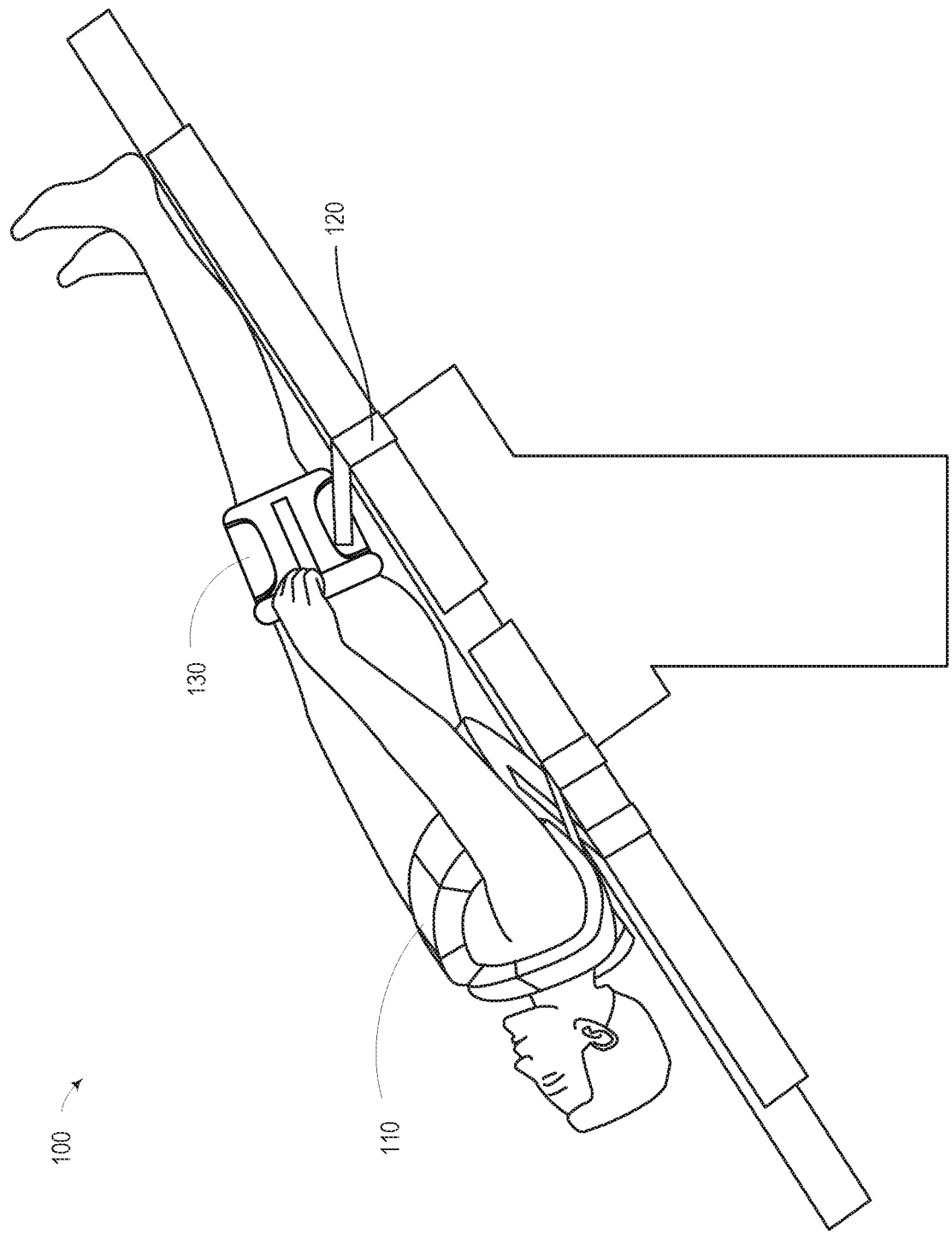
FIG. 3 depicts an example patient restraint system secured to a table in accordance with at least one embodiment.

Patient restraining system 100 further includes an attachment mechanism 120 designed to secure the patient to the table (e.g., operating table, surgical bed, or the like) when the patient is secured within the restraints 110, 130. FIG. 2 and FIG. 3 illustrate two example attachment mechanisms 120 of the system 100. The attachment mechanism 120 is coupled to (e.g., physically connected to or configured for physical coupling with) at least the upper body restraint 110 and the table. Additionally or alternatively, the attachment mechanism 120 (e.g., the same attachment mechanism or a further attachment mechanism) can be coupled to the lower body restraint 130. The attachment mechanism 120 reversibly secures the upper body restraint 110 to the table such that the position of the patient's chest is in a fixed position relative to the table when the attachment mechanism 120 is coupled to the upper body restraint 110 and the table. An attachment mechanism 120, which can be the same attachment mechanism or a further attachment mechanism, can reversibly secure the lower body restraint 130 to the table such that the position of the patient's leg is fixed relative to the table when the attachment mechanism is coupled to the lower body restraint 130 and the table. Such an attachment mechanism 120 can hold the patient in a fixed position by way of a tensile force along one or more straps forming the attachment mechanism 120. Additionally or alternatively, a frictional force between the patient and the table, the attachment mechanism 120 and the table, and/or the attachment mechanism 120 and the upper and lower body restraints 110, 130 can also secure the patient relative to the table.

The attachment mechanism 120 can be designed to secure patients of any size, for instance, patients weighing 250 lbs or less, patients weighing 300 lbs or less, patients weighing 330 lbs or less, patients weighing 400 lbs or less, patients weighing 1000 lbs or less, or some other weight. Accordingly, the attachment mechanism 120 can include a material selected for its strength, durability, elasticity (or lack thereof), or some other property. In one example embodiment, the attachment mechanism includes a nylon strap, for instance, ballistic nylon. In further examples, the attachment mechanism 120 includes an outer sheath of elastic spacer mesh, high-density foam, or some other material in order to improve comfort and/or frictional properties of the attachment mechanism 120.

In some examples, the attachment mechanism 120 includes one or more straps that extend between the upper body restraint 110 and/or lower body restraint 130 and the table, thereby holding the patient in a fixed position. As seen in FIG. 2, in some examples the attachment mechanism 120 includes at least one strap coupled to (i.e., connected to or configured for physical coupling with) at least the upper body restraint 110 and a table. For instance, in one embodiment the attachment mechanism 120 includes two straps (e.g., a left and right side strap) connectable to the upper body restraint 110. In yet further embodiments, the attachment mechanism 120 can include four straps, six straps, eight straps, or any desired number of configured to extend between the upper body restraint 110 and the table. In various embodiments, the attachment mechanism 120 is coupled to and/or connectable with the upper body restraint 110 at an outer shell of the restraint, a strap of the restraint, or some other element of the upper body restraint 110.

The strap(s) of the attachment mechanism 120 include a proximal end configured to attach to the upper body restraint 110 or the lower body restraint 130 and a distal end configured to attach to the table. In variable embodiments, the straps can be permanently fixed to (e.g., forming an integral part of) the upper body restraint 110, the lower body restraint 130 and/or the table, and can have an opposite "free" (i.e, not fixed) end for reversible securement via a fastener 122. As illustrated in FIG. 2, in one example embodiment, the attachment mechanism 120 is fixed to the upper body restraint 110, wherein the attachment mechanism 120 is either physically connected to or forming an integral part of the upper body restraint 110, and includes a fastener 122 at its distal end. Additionally or alternatively, an attachment mechanism 120 is fixed to the lower body restraint 130, and includes an additional fastener at its distal end. In various embodiments, the fastener(s) include buckles, hook-and-loop fasteners, loop connectors, non-conductive fasteners, parachute clips, or some other fasteners capable of reversible securing the attachment mechanism 120 to the table. In an exemplary embodiment, the material of the fastener includes a plastic or some other material selected to limit electrical conductivity and/or radiopacity. The attachment mechanism(s) 120 can be removably attachable to the table by way of the fastener(s) 122, such that the patient can be readily secured and released from the table by attaching and detaching the fastener(s) 122. In such examples, the upper body restraint 110 and/or the lower body restraint 130 can include a pocket or another means for arranging the attachment mechanism 120 and maintaining it in an away position when not in use.

In a contrasting embodiment, the attachment mechanism 120 is included as an integral part or add-on feature to the table, and the patient can be fastened into the table by securing the attachment mechanism 140 to the upper body restraint 110 and/or lower body restraint 130. More particularly, the attachment mechanism 120 can be fixed to the table at its distal end, and removably attachable to the upper body restraint 110 and/or lower body restraint 130 by way of a fastener on its proximal end.

In yet a further embodiment, the attachment mechanism 120 forms an intermediate between the upper body restraint 110 and the table, e.g., as a removable or standalone strap attachable to both the upper body restraint 110 and the table. In such an embodiment, the attachment mechanism 120 can form a selectively removable section (e.g., strap) of the upper body restraint 110 or some other portion of a harness and/or restraint system provided by the present disclosure. A further attachment mechanism (i.e., the same attachment mechanism 120 or an additional attachment mechanism) can be attachable to both the lower body restraint 130 and the table). In such examples, the attachment mechanism 120 includes a strap with fasteners at both its proximal and distal ends. The fastener at the proximal end can be removably attachable to either the upper body restraint 110 or the lower body restraint 130 and the fastener at the distal end can be removably attachable to the table.

In some embodiments, such as the embodiment illustrated in FIG. 3, the attachment mechanism 120 includes a strap configured to wrap around a table or a portion of a table (e.g., a railing of a surgical bed or a clamp attached to the table) and at least a portion of the upper body restraint 110 to secure the patient to the table. The same attachment mechanism 120 or an additional attachment mechanism can be provided which includes a strap configured to wrap around the operating table and at least a portion of the lower body restraint 130. More specifically, the attachment mechanism 120 includes an adjustable ratchet strap that can be tightly wound around the table and looped through at least a portion of the upper body restraint 110 (at, e.g., a loop or strap of the upper body restraint 110). In some examples, the system 100 can include multiple attachment mechanisms 120 coupled to or connectable with one or more portions of the upper body restraint 110.

While portions of the preceding paragraphs have described the attachment mechanism 120 principally in relation to the upper body restraint 110, it will be understood that the attachment mechanism 120 (or a further attachment mechanism) can be additionally connectable to the lower body restraint 130 and the table. An attachment mechanism 120 related to the lower body restraint 130 can include the same features, variations, connections, materials, and other characteristics described above in relation to the attachment mechanism related to the upper body restraint 110.

Figure 4:
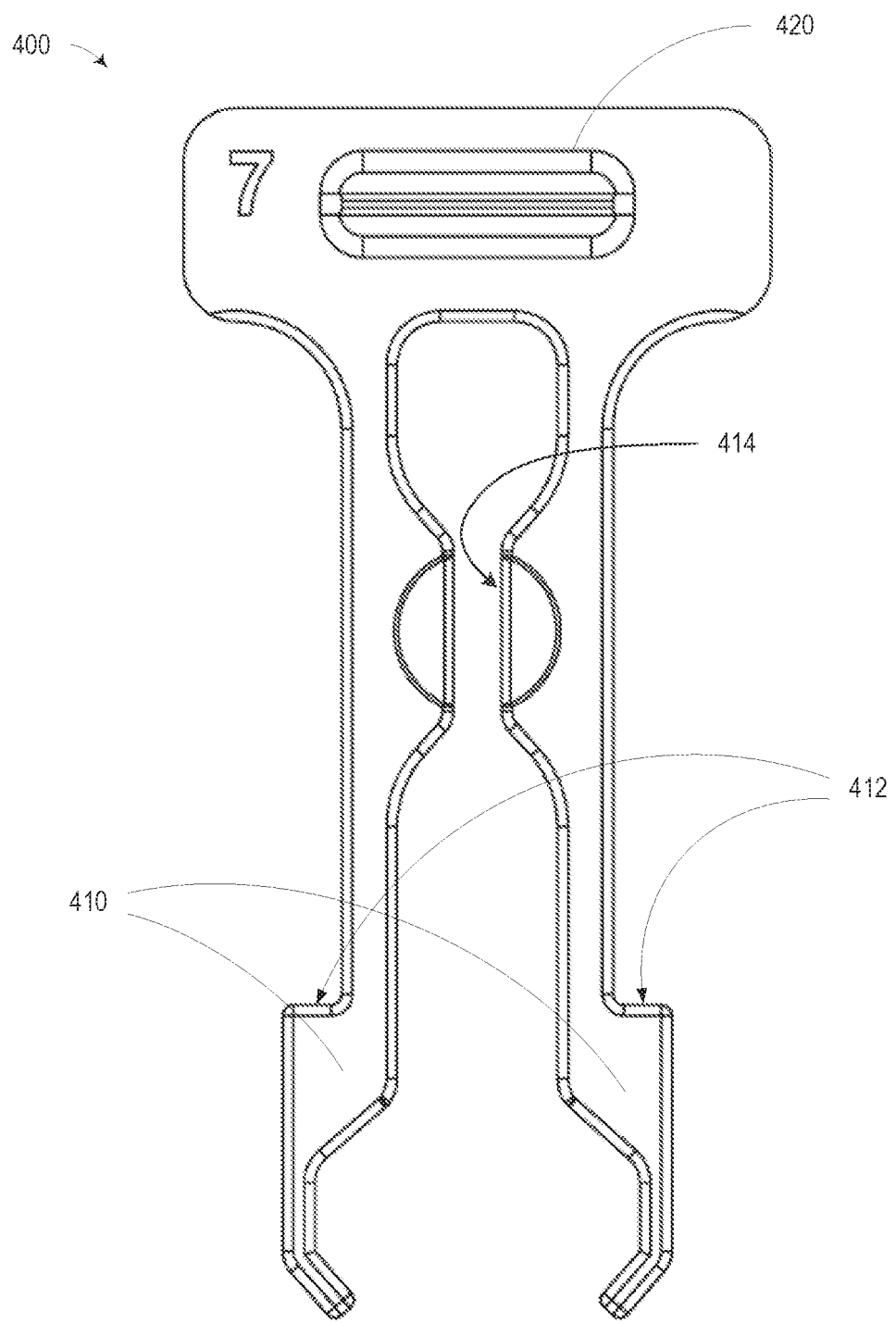
FIG. 4 depicts an example clip of an attachment mechanism in accordance with at least one embodiment.

System 100 can further include an intermediate connector to facilitate attachment of the attachment mechanism 120 to a table or surgical bed. For instance, the attachment mechanism 120 can be attachable to a portion of a table (e.g., a railing of a surgical bed), a clamp (e.g., a bed rail clamp) coupled to the table, or some other intermediate connector. In a particular example, the attachment mechanism 120 can be configured for use in conjunction with a Hill-Rom bed rail clamp. As seen in FIG. 4, in some examples the intermediate connector includes a clip 400. In such examples, the attachment mechanism is configured to couple to the table via the clip 400. Advantageously, such a clip 400 can allow for standardized attachment of the attachment mechanism 120, the upper restraining portion 110, and/or the lower restraining portion 130 to a variety of surfaces, i.e., any surface that permits coupling with the clip 400.

The clip 400 can be shaped to be used in conjunction with a patient care surface, for instance, by being attachable to a table and/or surgical bed or a portion thereof (e.g., a railing of the table). In an exemplary embodiment, the clip 400 includes two gripping members 410, and an attachment loop 420. In some examples, the two gripping members 410 are shaped to receive a railing of a table or an intermediate device connected to the table (e.g., a bed rail clamp). As seen in FIG. 4, the gripping members 410 can include prong-like structures spaced such that the distance between the two gripping members is approximately equal to a diameter of the railing of the table, a diameter of a clamp attached to the table, etc. In this context, "approximately equal" to the diameter indicates that the distance between the gripping members 410 is such that a railing or bed clamp can be fit snugly into the clip 400 such that the clip 400 does not slide or move when the clip 400 is engaged onto the railing.

In certain embodiments, the gripping members 410 can include one or more step features 412 that facilitate attachment of the clip to a bed rail clamp. The step feature(s) 412 can be formed as one or more outward protrusions on one or more of the gripping members 310. The protrusions can be oriented outwardly from the gripping member 410, thereby increasing a width of the gripping members 410 at the location of the step features 412. Accordingly, when the clip 400 is engaged (i.e., attached to or inserted within a railing and/or bed rail clamp), a railing can be positioned between the gripping members 410, and the step features 412 can function to prevent unintended removal of the clip 400 from the clamp. The step features 412 can additionally provide an audible "click" when the clip has been attached to the table railing or bed rail clamp, thereby alerting a user when the clip 400 has been fully engaged. In some examples, the gripping members 410 of the clip 400 extend past the bottom of the bed rail clamp when the griping members 410 are engaged with the bed rail clamp. Such a configuration facilitates removal of the clip by allowing a user of the clip to squeeze together the gripping members 410 to release the clip 400 from the bed rail clamp. A flared out shape can additionally be provided at the end of the gripping members 410 to make it easier and more ergonomic to squeeze the members and disengage the clip 400 from the bed rail clamp.

Additionally or alternatively, the gripping members 410 can include a wider section that provides a clamping surface 414 for a bed rail clamp to engage with. The clamping surface 412 can engage with the bed rail clamp and a railing by securing to the railing whben the clip is inserted in the bed rail clamp and a screw is inserted through a portion of the gripping members 410. When the clip 400 is inserted in a bed rail clamp and engaged by way of a screw or some other engagement mechanism, the clamping surface 412 is configured to secure around a portion of a railing of a table, thereby preventing the rail clamp from sliding along the railing. A dimple feature on the clamping surface 412 can further cause the gripping members 410 of the clip 400 to lock in their widest position when the bed rail clamp screw is engaged. Accordingly, when the clip 400 is engaged (i.e., attached to a railing or bed rail clamp), the railing can be positioned between the gripping members 410, and the step features 412 can function to prevent unintended removal of the clip 400 from the bed rail clamp.

In order to permit coupling of the attachment mechanism 120 to the clip 400, the clip 400 can further include an attachment eye 420 that allows for insertion of a portion of the attachment mechanism 120 through the clip 400. The attachment eye 420 of the clip 400 can be formed as a channel through the clip 400 that is shaped to permit attachment of the attachment mechanism 120. In examples wherein the attachment mechanism 120 includes a strap or plurality of straps (e.g., a flat nylon strap or some other tensile member), the attachment eye 420 can include a channel shaped to receive a strap (e.g., a longitudinal channel). The attachment eye 420 can further include features that secure the attachment mechanism 120 to the clip 400 when the attachment mechanism 120 is inserted through the attachment 420. For instance, the attachment eye 420 can be configured to cinch or clamp down on a strap of the attachment mechanism to enable a user to adjust a length of the attachment mechanism 120 and/or remove slack from the straps with one hand. Advantageously, this would facilitate securement of the patient and upper body restraint 110 to a table by allowing for easier coupling and tightening of the attachment mechanism 120 and, accordingly, the restrained patient.

The patient restraint system 100 can additionally include further features and functionalities to expedite surgical setup and/or aid in patient comfort. For example, in some embodiments the upper body restraint 110 and/or lower body restraint 130 includes a warming component configured to selectively provide warmth to the patient. The warming component can provide sufficient warmth maintain the patient's body temperature at or above a safe temperature during a surgical procedure (e.g., a predetermined temperature selected by a medical professional). The warming component can be configured to apply heat to the patient when the patient is secured within the upper and/or lower body restraint. The warming component can further include heated wires and/or conduits configured to accept a heated fluid, such as hot air, hot water, or another heated fluid.

The system 110 can additionally include at least one vascular circulation element to stimulate blood flow in a patient and prevent blood clotting during a surgical procedure. Such a vascular circulation element can be configured to sequentially compress a patient's blood vessel to mimic peristaltic pumping of blood. In one example, the vascular circulation element is included in the lower body restraint 130, and is configured to sequentially compress a blood vessel on the patient's leg, such as a vessel in the patient's thigh, calf, groin, ankle, or some other area. The vascular circulation element can also be defined by a circulation boot intended to be worn on the patient's foot, and can be optionally coupleable to the lower body restraint 130 via a strap or some other connector. In yet further embodiments, the vascular circulation element is included in the upper body restraint 110 and sequentially compresses a blood vessel proximate the upper body restraint 110.

The example implementations presently disclosed are not meant to be limiting. Components presently disclosed and illustrated in the figures can be arranged, substituted, combined, separated, and designed in a wide variety of different configurations, all of which are contemplated in the present disclosure.

Example Methods

Figure 5:
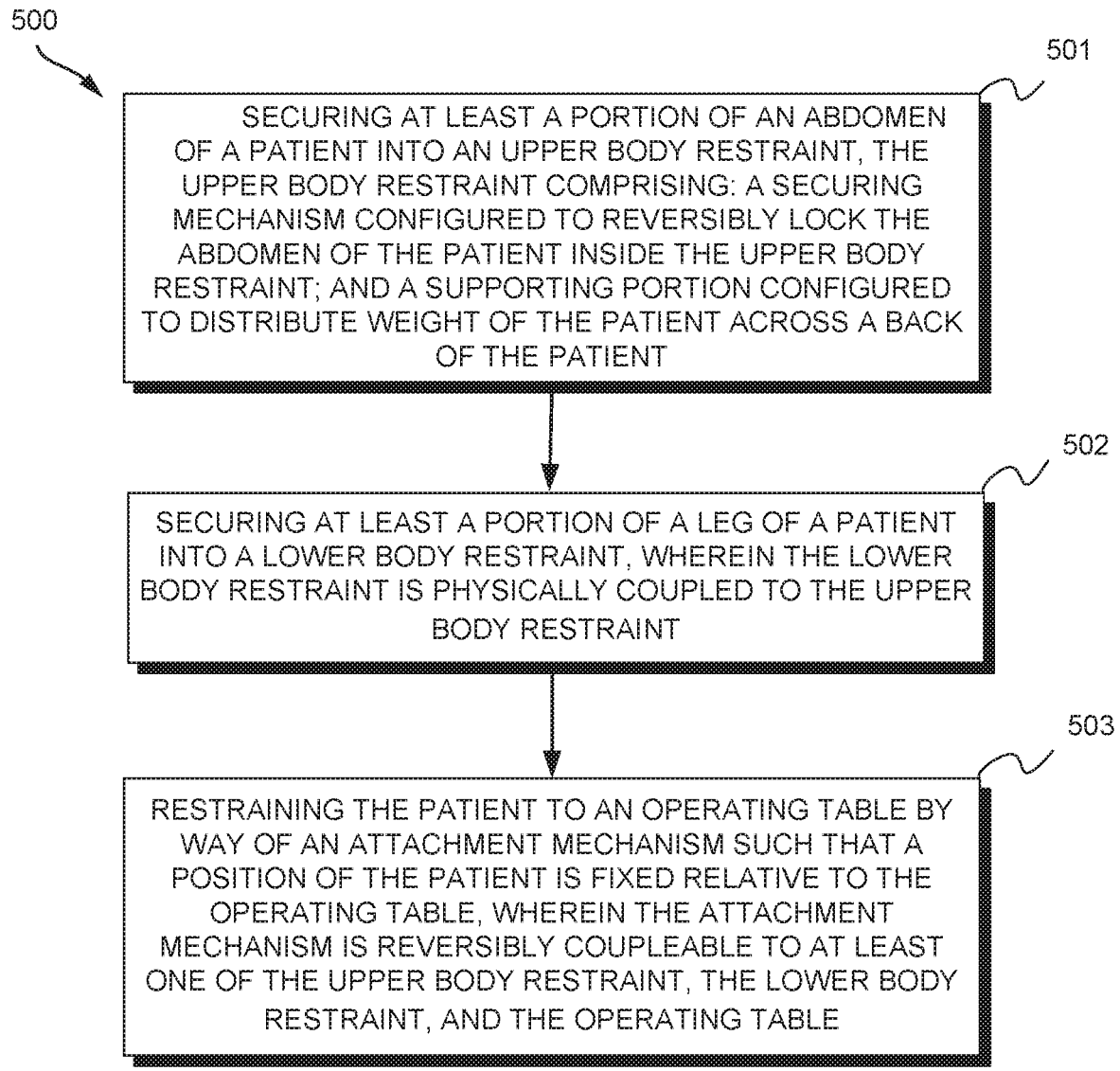
FIG. 5 depicts a flowchart of a method of restraining a patient during surgery in accordance with at least one embodiment.

FIG. 5 depicts a flowchart of a method 500 of restraining a patient during surgery in accordance with at least one embodiment. The method can be completed using a patient restraining system, such as any of the systems shown in FIGS. 1A-B, 2, and 3 and described herein. For purposes of illustration, the patient restraining system used in method 500 could include an upper body restraint, a lower body restraint, and an attachment mechanism. The upper body restraint includes a securing mechanism configured to reversibly lock such that the patient's chest is secured inside the upper body restraint; and a supporting portion configured to distribute the patient's weight across the patient's back.

Block 501 of method 500 includes configuring a device for securing at least a portion of patient's chest into an upper body restraint, such as the upper body restraint 110 of system 100. Securing the patient into the upper body restraint can include positioning the upper body restraint around the patient's torso, abdomen, neck, shoulders, and/or arms, such that the upper body restraint surrounds at least a portion of the patient's chest. In some examples, securing at least a portion of the patient's chest into the upper body restraint includes positioning one or more members of the upper body restraint into the securing mechanism.

Block 502 of method 500 includes configuring a device for securing at least a portion of a patient's leg into a lower body restraint, such as the lower body restraint 130 of system 100. The lower body restraint is physically coupled to the upper body restraint. e.g., by way of a strap or some other tensile member extending between the restraints.

Block 503 of method 500 includes configuring a device for restraining the patient to a table by way of an attachment mechanism, such as the attachment mechanism 120 of system 100. The attachment mechanism is capable of being reversibly coupled to at least one of the upper body restraint, the lower body restraint, and the table. The attachment mechanism positions the patient on the table in a fixed position, and is removably attachable to at least one of the upper body restraint, the lower body restraint, and the table.

Figure 6:
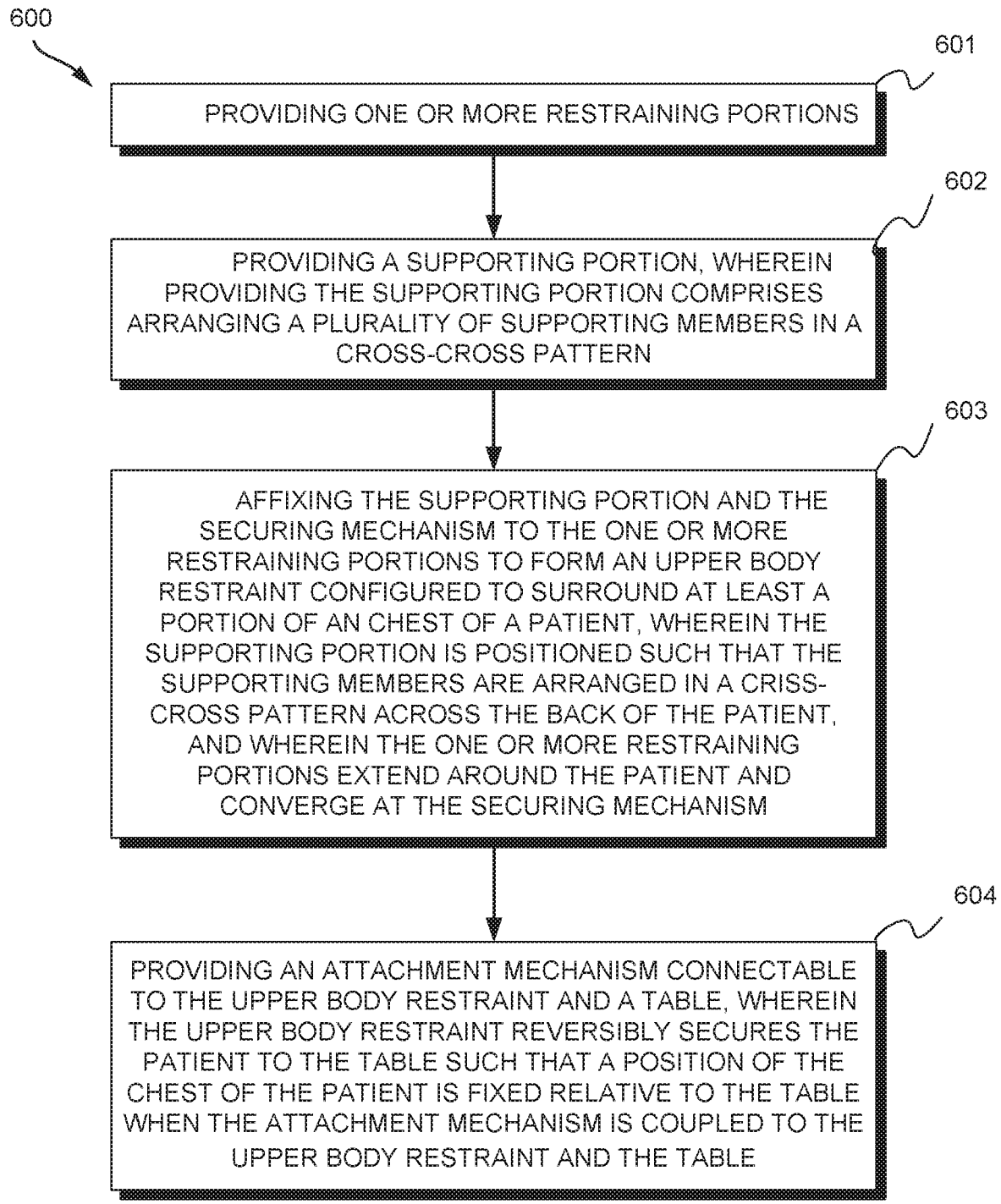
FIG. 6 depicts a flowchart of a method of manufacturing a patient restraining system in accordance with at least one embodiment.

Portions of the method 500 can occur before the patient has entered the operating room in order to save time during surgical setup. For instance, a nurse, an emergency professional, or the patient they can complete one or more steps of the method before the patient has entered the operating room, and a surgeon or surgical staff can complete the remaining steps of the method 500 once the patient has entered the operating room and is ready for surgery. Completing a portion of the method before beginning surgery can reduce setup time for a surgeon and reduce the patient's time under anesthesia, saving the hospital time and money. In a particular example, the patient can secure at least a portion of their own abdomen into the upper body restraint and secure at least a portion of their own legs into the lower body restraint, for example, in a waiting room before surgery. A surgeon or surgical staff can then proceed to restrain the patient to the table by way of the attachment mechanism FIG. 6 provides a method of manufacturing a patient restraining system, for instance, the patient restraining system 100 illustrated in FIGS. 1A-B, 2, and 3 and described herein. Block 601 of method 600 includes providing one or more restraining portions, such as the first restraining portion 111 and the second restraining portion 113 of the upper body restraint 110 of system 100. The one or more restraining portions could include members, e.g., straps, supports, or other restraining members made of ballistic nylon, elastic spacer mesh webbing, or some other material. In various alternative embodiments the upper body restraint 110 includes four restraining members, six restraining members, eight restraining members, or more.

Block 602 of method 600 includes providing a supporting portion. In some examples, the supporting portion 114 includes a plurality of supporting members (e.g., elastic or inelastic straps and/or other members configured to transfer tension in a longitudinal direction across the members). Providing the supporting portion can therefore include arranging a plurality of supporting members in a cross-cross pattern. The supporting members and larger supporting portion 114 can be formed of any desired material, for instance, nylon (e.g., ballistic nylon or military grade nylon), elastic spacer mesh, a textile, a polymer, or some other material.

Block 603 includes providing a securing mechanism. The securing mechanism can be configured to reversibly couple with one or more restraining portions and/or restraining members of the device (i.e., secure or lock itself in connection with the restraining portions or members). In various embodiments, the securing mechanism 112 includes a releasable buckle, such as a multiple-point buckle (e.g., a three point, four point, or five point buckle or the like), a loop connector, a hook-and-loop fastener, a snap fit connector, a parachute clip, or some other reversible securing mechanism.

Block 604 of method 600 includes affixing the supporting portion and the securing mechanism to the one or more restraining portions to form an upper body restraint. The upper body restraint can be configured similarly to the upper body restraint 110 illustrated in FIGS. 1, 2, and 3 and described herein. For instance, the upper body portion can be configured to surround at least a portion of a patient's chest, with the securing mechanism generally located on the patient's front size (i.e., proximate to the chest and/or abdomen) and the supporting portion generally positioned such that the supporting members are arranged in a criss-cross pattern across the patient's back. The restraining portions can be affixed whereby they that extend from the supporting portion proximate to the patient's back, around the patient's arms and/or shoulders, and converge at the securing mechanism. In a particular example, the upper body restraint 110 can be configured similarly to a vest-like garment, including restraining portions configured to extend over the patient's shoulders and/or under the patient's armpits, leaving uncovered the patient's upper extremities.

Block 605 of method 600 includes providing an attachment mechanism, such as the attachment mechanism 120 of system 100. The upper body restraint reversibly secures the patient to the table, wherein the patient's chest is in a fixed position relative to the table when the attachment mechanism is coupled to the upper body restraint and the table. In some examples, the attachment mechanism 120 includes one or more straps that extend between the upper body restraint 110 and/or lower body restraint 130 and the table, thereby holding the patient in a fixed position. The straps can be affixed to the upper body restraint such that they form an integral part of the upper body restraint, and can have an opposite "free" (i.e, not fixed) end for reversible securement to the table. However, in other examples the attachment mechanism forms an intermediate between the upper body restraint and the table, e.g., as a removable or standalone strap attachable to both the upper body restraint and the table. The attachment mechanism can be directly connectable to the upper the table, or alternatively, can attach to a clip (e.g., clip 400), a bed rail clamp, or some other intermediate device attached to the table.

The example methods 500 and 600, illustrated in FIGS. 5 and 6 respectively, are meant as an illustrative, non-limiting examples. Blocks and steps described herein can be carried out sequentially or in parallel. Furthermore, the various blocks and steps can be carried out in a different order than described herein and some steps can be omitted, skipped, and/or repeated. Additional or alternative elements of the methods 500 and 600 and additional or alternative components of the system 100 are anticipated, as will be obvious to one skilled in the art.

The above detailed description describes various features and functions of the disclosed systems, devices, and methods with reference to the accompanying figures. While various aspects and embodiments have been disclosed herein, other aspects and embodiments will be apparent to one having skill in this art. The various aspects and embodiments disclosed herein are for purposes of illustration only and are not intended to be limiting, with the true scope being indicated by the following claims.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be used, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A system for restraining a patient before, during, or after surgery, the system comprising:
   an upper body restraint configured to surround at least a portion of a chest of the patient, the upper body restraint comprising:
      a first annular restraining portion configured to encircle a neck of the patient and comprising straps configured to extend over shoulders of the patient and downwards along a back of the patient;
      a second restraining portion configured to encircle the chest of the patient and to extend under armpits of the patient;
      a securing mechanism, wherein the securing mechanism is configured to directly and reversibly lock the first restraining portion to the second restraining portion such that the chest of the patient is configured to be reversibly secured within the upper body restraint;
      a supporting portion configured to distribute weight of the patient across a torso of the patient; and attachment mechanisms extending laterally from the straps of the upper body restraint for selectively securing the upper body restraint to a table, wherein the upper body restraint is configured to reversibly secure the patient to the table, and when the attachment mechanisms are connected to the upper body restraint and the table, the patient's abdomen is in a fixed position on the table.

2. The system of claim 1, further comprising:
a lower body restraint configured to surround at least a portion of a leg of the patient and to connect to the upper body restraint;
wherein when the lower body restraint is connected to the upper body restraint, the patient's leg is in a fixed position on the table.

3. The system of claim 2, wherein the lower body restraint further comprises at least one vascular circulation element configured to sequentially compress a blood vessel of the patient to prevent blood clotting.

4. The system of claim 1, wherein the securing mechanism comprises one or more releasable buckles.

5. The system of claim 4, wherein the one or more releasable buckles comprises a multiple point buckle.

6. The system of claim 1, wherein each attachment mechanism comprises a strap including a proximal end configured to attach to the upper body restraint and a distal end configured to attach to the table, and wherein at least one of the proximal end and the distal end includes a fastener.

7. The system of claim 6, wherein the fastener comprises at least one of a buckle, a non-conductive fastener, and a hook-and-loop fastener.

8. The system of claim 1, wherein each attachment mechanism is fixed to the upper body restraint and is removably attachable to the table by way of the fastener.

9. The system of claim 1, wherein each attachment mechanism comprises:
a strap extending between the upper body restraint and the table; and
a clip, wherein each attachment mechanism is configured to couple to the table via the clip.

10. The system of claim 9, wherein the clip comprises:
two gripping members shaped to receive a railing of the table; and
an attachment eye shaped to receive the strap.

11. The system of claim 1, wherein at least a portion of the upper body restraint is adjustable to increase or decrease a size of the upper body restraint.

12. The system of claim 1, wherein the supporting portion comprises a plurality of supporting members configured to be arranged in a criss-cross pattern across the back of the patient.

13. The system of claim 1, wherein a plurality of supporting members comprises elastic spacer mesh webbing.

14. The system of claim 1, wherein at least a portion of the upper body restraint comprises ballistic nylon.

15. The system of claim 1, wherein at least a portion of the upper body restraint comprises a high-density foam.

16. The system of claim 1, further comprising at least one warming component configured to apply heat to the patient when the patient is secured within the upper body restraint.

17. A method of manufacturing a patient restraining system according to claim 1, the method comprising:
providing one or more restraining portions that include the first restraining portion and the second restraining portion;
providing the supporting portion, where providing the supporting portion comprises arranging A plurality of supporting members in a criss-cross pattern;
providing the securing mechanism configured to reversibly couple with the one or more restraining portions;
affixing the supporting portion and the securing mechanism to the one or more restraining portions to form the upper body restraint configured to surround at least the portion of the chest of the patient, wherein the one or more restraining portions extend around the patient and converge at the securing mechanism such that the first restraining portion encircles the neck of the patient and extends over the shoulders of the patient, the second restraining portion encircles the chest of the patient and extends under the armpits of the patient, and the securing mechanism reversibly locks the first restraining portion to the second restraining portion such that the chest of the patient is reversibly secured within the upper body restraint; and
providing the attachment mechanisms connectable to the upper body restraint and the table, wherein the upper body restraint reversibly secures the patient to the table wherein the chest of the patient is in a fixed position relative to the table when the attachment mechanisms are coupled to the upper body restraint and the table.

18. A method of restraining a patient during surgery, the method comprising:
securing at least a portion of a chest of the patient into an upper body restraint, the upper body restraint comprising:
a first annular restraining portion configured to encircle a neck of the patient and comprising straps configured to extend over shoulders of the patient and downwards along a back of the patient;
a second restraining portion configured to encircle the chest of the patient and to extend under armpits of the patient;
a securing mechanism configured to directly and reversibly lock the first restraining portion to the second restraining portion such that the chest of the patient is secured within the upper body restraint; and
a supporting portion configured to distribute weight of the patient across aback of the patient;
securing at least a portion of a leg of the patient into a lower body restraint, wherein the lower body restraint is coupled to the upper body restraint; and
restraining the patient to a table by way of attachment mechanism& that extend laterally from the straps of the upper body restraint and position the patient on the table in a fixed position, wherein the attachment mechanisms arm removably attachable to at least one of the upper body restraint, the lower body restraint, and the table.

* * * * *